United States Patent [19]

Bell

[11] Patent Number: 4,529,396
[45] Date of Patent: Jul. 16, 1985

[54] APPARATUS FOR FORMING A ROLLED TUBULAR FABRIC ARTICLE

[75] Inventor: Hank Bell, Dallas, Tex.

[73] Assignee: Hydro-Med Products, Inc., Dallas, Tex.

[21] Appl. No.: 435,749

[22] Filed: Oct. 21, 1982

[51] Int. Cl.³ .................... B31C 13/00; B65B 63/04
[52] U.S. Cl. ................................ 493/244; 493/252; 493/423; 493/462; 493/938; 53/117; 53/430
[58] Field of Search .................. 26/84, 85; 29/235; 53/117, 118, 204, 409, 430, 567, 581; 414/755; 493/243, 244, 250, 407, 409, 410, 422, 423, 436, 461, 462, 967, 252, 937, 938

[56] References Cited

U.S. PATENT DOCUMENTS

| Re. 30,410 | 10/1980 | Povlacs | 414/755 X |
| 2,892,297 | 6/1959 | Derrah et al. | 53/245 X |
| 3,007,195 | 11/1961 | Gammeter | 29/235 |
| 3,588,997 | 6/1971 | Field | 29/235 X |
| 3,610,115 | 10/1971 | Rose et al. | 493/423 |

FOREIGN PATENT DOCUMENTS

| 1422451 | 11/1965 | France | 493/423 |
| 2059477 | 4/1981 | United Kingdom | 26/84 |

Primary Examiner—John Sipos
Assistant Examiner—Steven P. Weihrouch
Attorney, Agent, or Firm—Kenneth R. Glaser

[57] ABSTRACT

An apparatus for rolling elongated tubular fabric surgical drapes and the like comprising an arrangement of at least four opposed drive belts mounted on a support frame for receiving an open end of the tubular article engageable with longitudinal runs of the belts to propel the article along the frame and into engagement with a second set of belts having longitudinal runs disposed at acute angles with respect to the direction of the runs of the primary drive belts. Propulsion of the end of the article along the primary drive belts and into engagement with the secondary drive belts results in forming the article into a toroidal rolled configuration. A support frame for the primary drive belts is mounted on a linear actuator which provides for movement of the support frame with respect to the secondary drive belts in response to operation of a control circuit to complete the rolling process. The separate sets of drive belts are driven by a single electric motor through separate drive trains including a disengageable clutch in the drive train for the primary belts. The apparatus may be controlled for automatic operation through a complete operating cycle of rolling and ejecting a tubular article from the apparatus.

8 Claims, 8 Drawing Figures

APPARATUS FOR FORMING A ROLLED TUBULAR FABRIC ARTICLE

BACKGROUND OF THE INVENTION

1. Field of the Invention

The present invention pertains to an apparatus for rolling a tubular fabric article such as a surgical drape into a toroidal roll for storage and application to a patient extremity.

2. Background

Certain types of tubular fabric articles are desirably formed into a rolled configuration so that they may be more easily stored and, upon application for use, unrolled as required. One type of tubular fabric article which is normally stored in a toroidal rolled state is a tubular drape for use in covering a patient extremity preparatory to and during surgical procedures. Surgical drapes are typically formed of a flexible material such as a knit fabric or a multilayer structure of knit and monosheet fabric. Such articles are desirably rolled into a toroid for convenience in storing the articles, to more easily maintain the articles in a sterile state, and to facilitate application of the article to a patient's extremity by unrolling the article from the distal end of the extremity over the area to be covered.

In the manufacture of tubular fabric articles such as surgical drapes the rolling of the article has heretofore been performed manually by placing the tubular article, after fabrication, on a mandrel or the like and manually rolling the open end of the article onto itself in a toroidal fashion until the article is rolled substantially toward its closed end. Accordingly, there has been a long felt need for apparatus which is capable of forming tubular fabric articles and the like into a toroidal roll wherein the convenience of storage of the article is enhanced, the sterilized condition of the article is more easily maintained, the tightness or size of the roll for an article of a given length is more closely controlled to facilitate packaging and storage, and the rate of production of such articles is substantially improved.

SUMMARY OF THE INVENTION

The present invention provides an apparatus for automatically forming an elongated tubular fabric article in a rolled configuration for storage and for application to the end use of the article. In particular, the apparatus of the present invention is particularly adapted for rolling elongated tubular fabric surgical drapes and the like.

In accordance with one aspect of the present invention there is provided an apparatus wherein a first set of drive members is arranged such that the tubular fabric article may be sleeved over the drive members of said first set and propelled toward a second set of drive members engageable with the distal end of the tubular article to roll the end back on itself to commence the formation of a toroidal rolled configuration of the article. The first and second sets of drive members are preferably formed as endless flexible belts which are engageable with the material of the tubular article to provide the feeding and rolling process. The first and second sets of drive members are arranged in a pattern of four opposed sets of endless belts which are suitably interconnected through drive mechanism to be rotated in unison by a drive motor and transmission means interconnecting the motor and the respective sets of drive members.

In accordance with another aspect of the present invention there is provided and apparatus which is operable to form a tubular fabric article such as a surgical drape into a toroidal roll wherein the article is rolled substantially throughout its entire length leaving a minimum unrolled portion to facilitate handling, storage and application of the article to a patient extremity, for example. In carrying out this aspect of the invention there is provided an apparatus wherein one set of drive members is longitudinally movable relative to another set of drive members so that the article which is being rolled by the apparatus may be rolled throughout substantially its entire length.

In accordance with yet another aspect of the present invention there is provided an apparatus which is automatically controllable to form the rolled shape of a flexible tubular article being worked by the apparatus and to complete the rolling cycle by moving one set of drive members relative to the other to complete the rolling process and to position the rolled article for easy access to remove the article from the apparatus itself. The rolling apparatus is operable to perform a complete cycle of driving first and second sets of drive members with respect to each other, initiating linear movement of one set of drive members relative to the other to roll the last portion of the article, return the first set of drive members to the starting position and operating the drive mechanism to shut-off to complete the operating cycle until the rolled article is removed from the apparatus.

Although most tubular surgical drapes are closed at one end this structural requirement is not necessary for application of the basic concept of the instant invention to rolling tubular flexible articles. Those skilled in the art will recognize the abovementioned aspects of the present invention as well as additional superior features and advantages upon reading the detailed description which follows in conjunction with the drawings.

DESCRIPTION OF THE PREFERRED EMBODIMENT

In the description which follows like parts are marked throughout the specification and drawings with the same reference numerals, respectively. The drawings are not necessarily to scale and certain features of the apparatus of the invention may be exaggerated in scale or depicted in schematic form for illustrative purposes in the interest of clarity and conciseness. The term fabric as used throughout the specification and claims is intended to mean a flexible material having the capability of being folded or otherwise manipulated generally in the manner of knitted or woven fabrics. For example, the term fabric may include flexible material which is formed of a solid sheet. Although the apparatus described herein may be utilized to form a variety of tubular articles of flexible material into a rolled toroid the apparatus is particularly adapted to be used in conjunction with rolling elongated tubular fabric articles such as surgical drapes and the like. One example of an article which may be rolled into a toroidal shape by the apparatus of the present invention is a surgical drape disclosed and claimed in U.S. Pat. No. 3,968,792 which is assigned to the assignee of the present invention.

Figure 1:
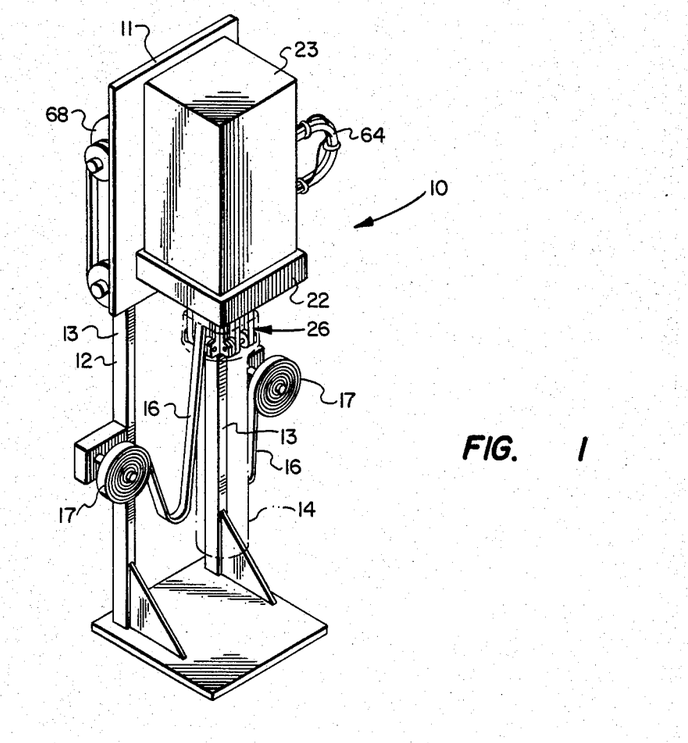
FIG. 1 is a perspective view of an apparatus for forming tubular fabric articles in a rolled configuration in accordance with the present invention.

Referring to FIG. 1 of the drawings there is illustrated an apparatus in accordance with the present invention and generally designated by the numeral 10. The apparatus 10 includes a support stand 12 having opposed upstanding legs 13 for supporting a base member 11 in such a way that an elongated tubular fabric member such as a surgical drape or the like 14, may be mounted on a portion of the apparatus in sleeved relationship thereover and hanging generally vertically downward from the apparatus as illustrated. If the rolled tubular article is to be furnished with pull straps, such as the straps 16 illustrated in FIG. 1, these are preferably attached at one end thereof to a point adjacent the open end of the tubular article whereupon, as the article is rolled into a toroid, the pull straps are also rolled to form a plurality of circular folds or layers which will facilitate unrolling the article and minimize the chances of touching the article by human hands. The straps 16 are fed to each drape 14 from opposed bulk strapping rolls 17 which are suitably mounted on the support stand 12, as illustrated.

Figure 2:
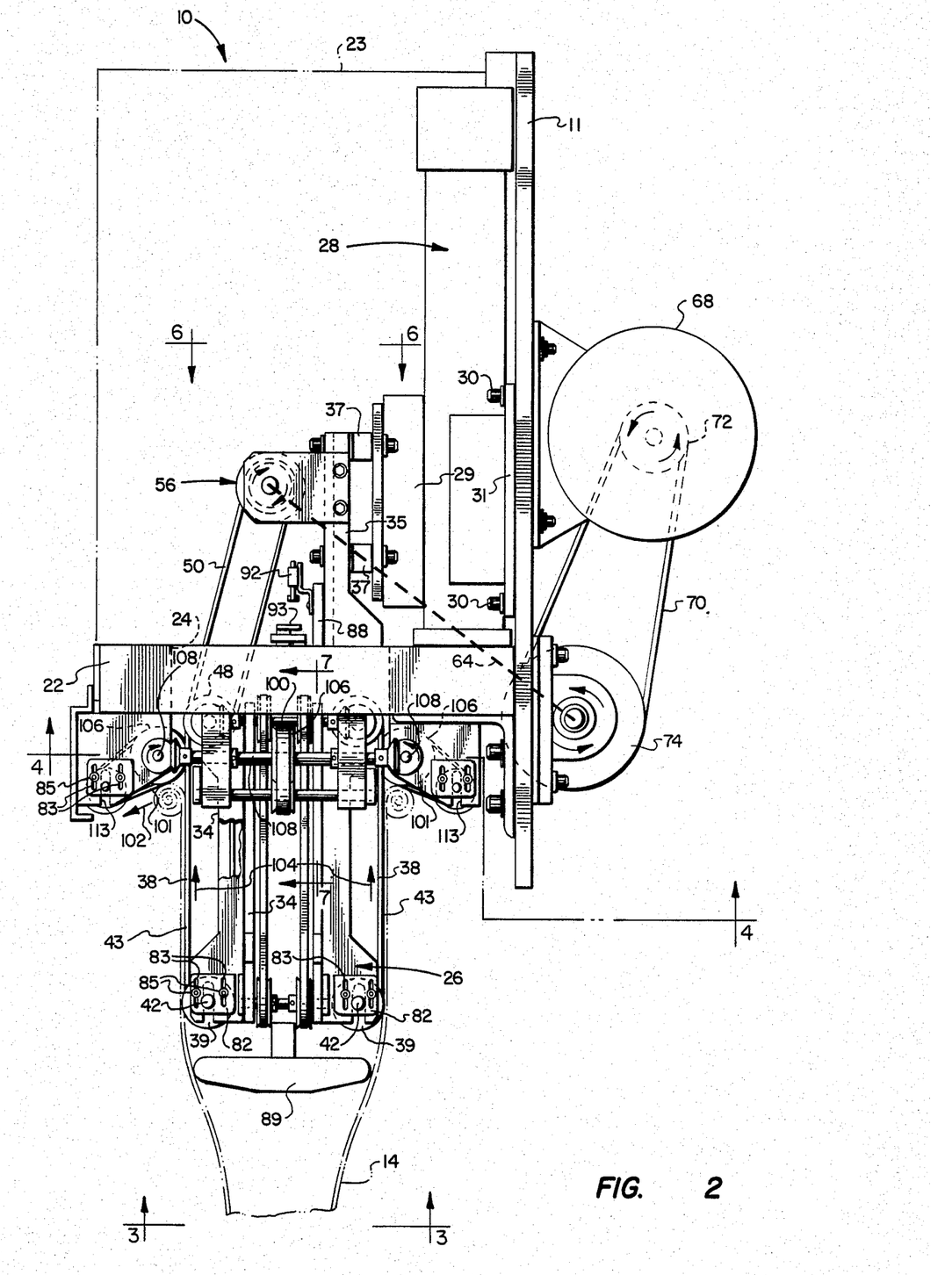
FIG. 2 is a longitudinal side elevation of the apparatus illustrated in FIG. 1.
Figure 3:
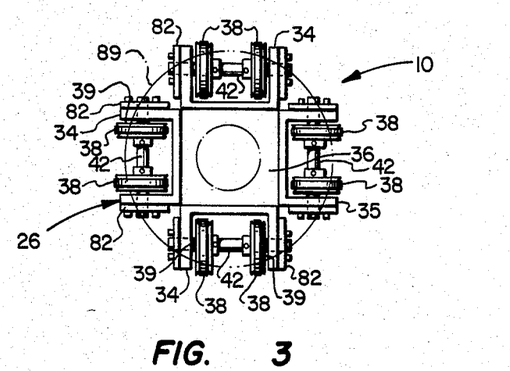
FIG. 3 is a view taken substantially from the line 3—3 of FIG. 2.
Figure 4:
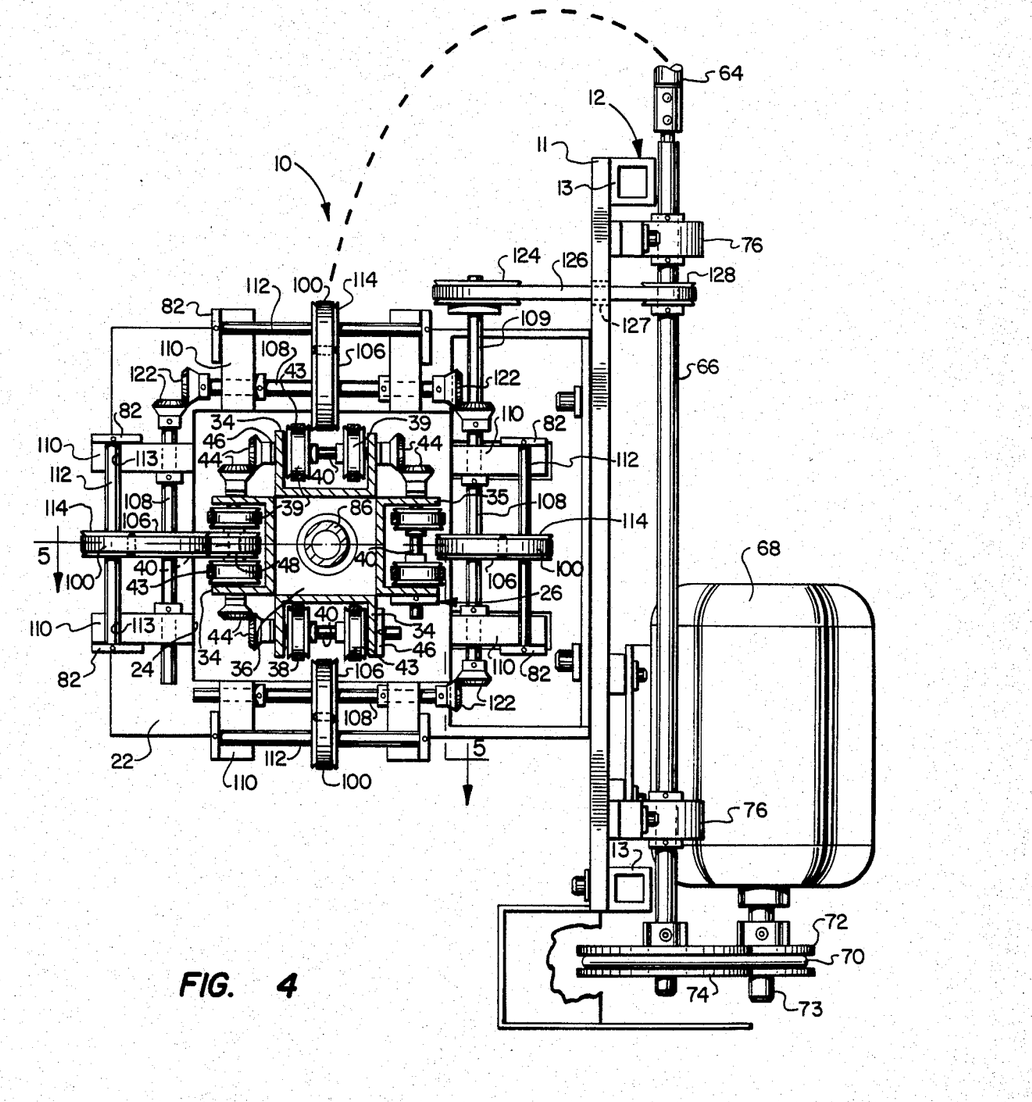
FIG. 4 is a section view taken substantially along the line 4—4 of FIG. 2.

Referring now to FIGS. 2, 3 and 4, the base member 11 is characterized as an elongated flat plate and includes a generally rectangular frame plate 22 secured to one face thereof and projecting generally perpendicular thereto. The frame plate 22 has a rectangular opening 24 formed therein to provide clearance for a linearly movable support frame, generally designated by the numeral 26. The support frame 26 is mounted on a linear reciprocable actuator, generally designated by the numeral 28, and disposed within a removable hood 23 mounted on the frame plate 22. The actuator 28 is, in turn, suitably supported on the base member 11 by spaced apart fasteners 30 which clamp a supporting frame member 31 for the actuator to the base member. The actuator 28 preferably comprises a double acting pressure fluid cylinder type actuator including a mounting slide member 29 which is suitably connected to the support frame 26 to reciprocate the support frame linearly in opposite vertical directions, viewing FIG. 2, in response to pressure fluid being admitted to one end or the other of the actuator cylinder. The particular cylinder type actuator 28 illustrated is a so-called rodless type which is commercially available. One source of such an actuator is a model P1205/22 made by the Origa Corporation, Elmhurst, Ill.

Figure 5:
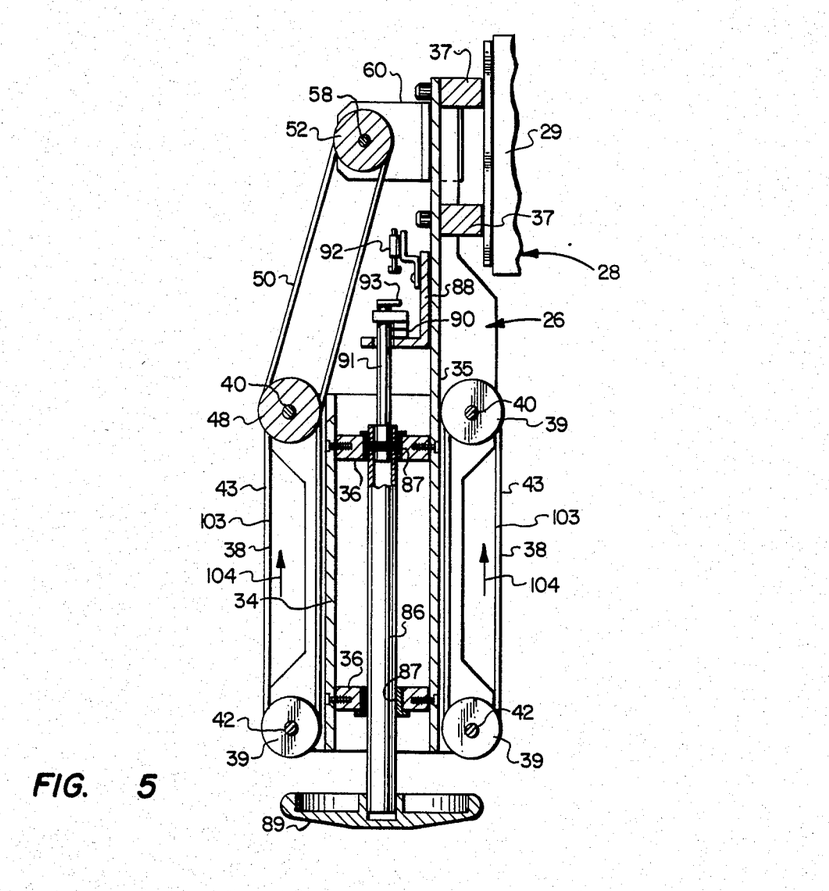
FIG. 5 is a detail section view of a portion of the apparatus and is taken along the line 5—5 of FIG. 4.

Referring further to FIGS. 3 and 4, the support frame 26 is characterized by a four opposed, elongated, channel shaped members 34 and 35 which are arranged in a rectangular pattern and are secured in assembly by being bolted to spaced apart frame plates 36, as shown in FIG. 5 also. The member 35 includes an end portion projecting beyond the other channel members and serving as means for securing the support frame 26 to the slide member 29 of the cylinder actuator utilizing two spaced apart support blocks 37, FIGS. 2 or 5. Each of the channel shaped members 34 and 35 are adapted to support drive means comprising a pair of elongated endless flexible drive belts 38 which are suitably spaced apart from each other and are supported for rotation on drive shafts 40 at one end of the support channels and idler shafts 42 rotatably mounted at the opposite end of the support channels. The belts 38 are trained over pulleys 39 mounted on and the shafts 40 and 42, respectively. The pulleys 39 on shafts 40 are drivenly connected to these shafts which rotate in suitable bearings in the channel members 34 and 35; however, the shafts 42 are stationary and the pulleys 39 are rotatable thereon. The belts 38 are preferably formed of a flexible elastomeric material having a relatively high coefficient of friction on the outer belt surfaces 43 which are engageable with the tubular article to be rolled by the apparatus 10.

Referring briefly to FIGS. 2 and 3, the idler shafts 42 are supported in spaced apart blocks 82 which are adjustably mounted on the flanges of the respective channel members 34 and 35 whereby the tension in the belts 38 may be selectively adjusted as desired. The blocks 82 are each provided with elongated slots 83, see FIG. 2, through which suitable socket head type threaded fasteners 85 project for clamping the blocks to the outside faces of the flanges of the channel members 34 and 35.

Referring particularly to FIG. 4, the drive shafts 40 are each rotatably supported between and by the opposed flanges of the channel members 34 and 35 which may, as previously mentioned include suitable antifriction or sleeve bearing elements for journalling the respective shafts. The shafts 40 are drivably interconnected to each other by intermeshing bevel gears 44 suitably mounted on opposed ends of two of the shafts 40 and on one end only of the other two of the shafts 40. The shafts 40 are each retained on the channel members 34 and 35 by the bevel gears 44 having thrust washers 46 interposed between their hubs and the flanges of the support channels. Accordingly, all of the belts 38 are adapted to be driven in unison, at the same surface speed and in the same direction along their outer linear runs between the shafts 40 and 42.

Figure 6:
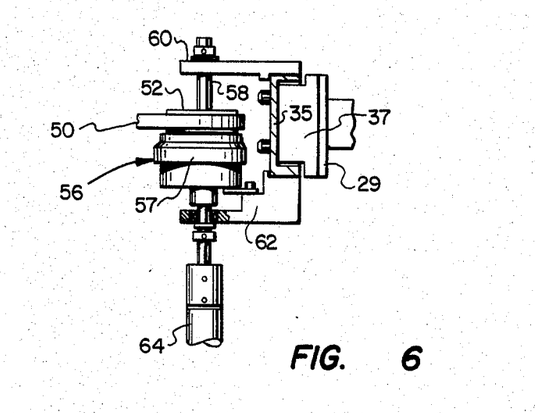
FIG. 6 is a detail view, partially sectioned, taken along the line 6—6 of FIG. 2.

Referring also to FIG. 5, the shaft 40 mounted on the channel 34 which is directly opposite the channel 35 includes a drive pulley 48 suitably secured thereto and mounted between the pulleys 39. The drive pulley 48 is in driven engagement with an endless belt 50 which is trained over a drive pulley 52, as shown in FIGS. 5 and 6. The drive pulley 52 comprises the driven member of an electromagnetic clutch, generally designated by the numeral 56 in FIG. 6. The clutch 56 is mounted on a shaft 58 disposed between a pair of bearing support members 60 and 62 which are suitably secured to opposed flanges of the channel member 35. The clutch 56 includes a driving member 57 which is secured to the shaft 58 for rotation therewith. The shaft 58 is in driven engagement with a flexible drive shaft, generally designated by the numeral 64 in FIG. 6. The opposite end of the flexible drive shaft 64 is drivenly engaged with a line shaft 66, as shown in FIG. 4, which in turn is arranged to be rotatably driven by a drive motor 68 mounted on the base member 11. The motor 68 is drivingly engaged with the shaft 66 through an endless drive belt 70 trained over respective driving and driven pulleys 72 and 74, respectively. The pulley 72 is mounted on and drivenly engaged by an output shaft 73 of the motor 68 and the pulley 74 is suitably mounted on and drivingly engaged with the line shaft 66. The line shaft 66 is mounted in spaced apart pillow blocks 76 disposed on the back side of the base member 11.

Referring again to FIG. 5, the apparatus 10 also comprises an elongated actuator shaft 86 which is slidably mounted in suitable sleeve bearings 87 disposed in respective ones of the spaced apart support plates 36. The actuator shaft 86 includes a generally circular disc shaped actuating pad member 89 connected to the lower end thereof and extending below the support frame 26. The actuator shaft 86 includes a longitudinally extending rodlike portion 91 which extends through a bracket 88 mounted adjacent the end of the shaft opposite the actuator pad 89 and adapted to support one portion of a magnetic latch, generally designated by the numeral 90. The latch 90 is similar to a conventional magnetic door latch and is adapted to releasably secure the actuator shaft 86 in the position shown in FIG. 5 but, in response to a predetermined upward axial force acting on the pad 89, will release the actuator shaft for linear translation upward, viewing FIG. 5, so that a trigger 93 mounted on the upper end of the actuator shaft can engage a limit switch 92. Since the actuator shaft 86 is mounted for linear reciprocating movement in a vertical direction the force of gravity acting on the shaft 86 is sufficient to bias it in the position illustrated in FIG. 5 absent a sufficient opposing force acting on the pad 89. The function of the actuator shaft 86 will be explained in further detail herein in conjunction with an explanation of the operation of the apparatus 10.

Figure 7:
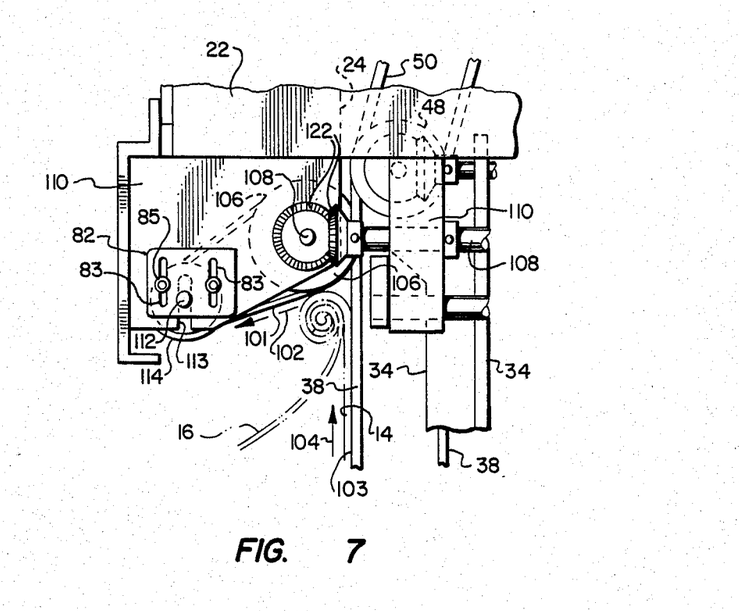
FIG. 7 is a detail view of one of the secondary drive belts taken from the line 7—7 of FIG. 2 and showing the leading end of a tubular article being rolled.

Referring again to FIGS. 2, 4 and also to the detail view of FIG. 7, the apparatus 10 includes a second set of drive members comprising endless flexible drive belts 100 which are adapted to be partially disposed between respective sets of the drive belts 38 and are suitably supported to have a generally linear belt run 101 extending generally radially outward with respect to the longitudinal central axis of the arrangement of drive belts 38 and the actuator shaft 86. The direction of movement of the respective belt runs 101 and 103 of the belts 100 and 38 are indicated by the respective arrows 102 and 104 in FIG. 7. FIG. 7 is representative of the relationship of each set of belts 38 and belt 100. The drive belts 100 are also disposed in a manner such that the linear belt runs 101 project at an acute angle with respect to the longitudinal extent of the belt runs 103. The belts 100 are each trained over drive pulleys 106 mounted on respective rotating drive shafts 108.

The drive shafts 108 are each mounted in spaced apart bearing blocks 110 which are supported by the frame plate 22. The bearing blocks 110 also support respective idler shafts 112 on which idler pulleys 114 are rotatably mounted in supportive relationship to the drive belts 100. The idler shafts 112 extend through recesses 113 in the blocks 110 and are suitably mounted in spaced apart adjustable blocks 82 which are secured to the sides of the blocks 110 by threaded fasteners 85 in a manner similar to the arrangement of the blocks for the idler shafts 42.

The drive shafts 108 are drivenly interconnected for rotation in unison by an arrangement of intermeshing bevel gears 122 as illustrated in FIG. 4. One of the drive shafts for the drive pulleys 106 includes an extended portion, designated by the numeral 109, and adapted to have a drive pulley 124 mounted thereon, over which pulley is trained a drive belt 126. The drive belt 126 is also trained over a drive pulley 128 mounted on and drivenly engaged with the line shaft 66, as shown in FIG. 4. The drive belt 126 extends through a suitable slot 127 formed in the base member 11.

As will be appreciated from the foregoing description the drive belts 38 and 100 are arranged to be driven in unison by the drive motor 68 through the respective drive trains described. Accordingly, with the support frame 26 in the position illustrated in FIG. 2 a tubular article such as the surgical drape 14 may be initially pulled over the end of the support 26 at which the pad 89 is disposed, in sleeved relationship thereto, and in engagement with the opposed sets of belts 38. Upon energization of the motor 68 and engagement of the clutch 56, the belts 38 are driven in the direction of the arrows 104 by way of the drive train comprising the belt 70, the line shaft 66, the flexible drive shaft 64, the clutch 56, the drive belt 50 and, of course, the respective interconnected drive shafts 40.

With the belt runs 103 engaged with the article 14 the article will be pulled along the belts in the direction of the arrows 104 until the distal end of the article engages the belts 100 along the runs 101 thereof. Since the runs 101 of the belts 100 are traveling in the direction of the arrows 102 the end of the tubular article 14, upon engagement with the belts 100, will tend to be splayed radially outward; however, the elasticity of the article fabric will cause the end to be rolled back on itself in a circular roll to commence formation of the toroid. It has been determined that it is important that the belt runs 101 be traveling at a linear surface speed greater than the runs 103 of the belts 38. In this way the toroidal roll is formed to the desired degree of tightness and the tendency to bunch or jam the tubular article against the belts 100 is avoided. The relative surface speeds of the belts 100 and 38 may be adjusted in accordance with the material of the tubular article and the coefficient of friction between the surfaces of the belt runs engageable with the article itself. Although the feed rate of the tubular article toward the belts 100 is less than the instantaneous linear surface speed of the runs 101 and some slippage occurs between the belts 100 and the surface of the article itself this has proved not to be detrimental to the material of the articles or to the drive belts 100.

The action of the drive belts 38 and 100 to roll the tubular article 14 into the toroidal rolled shape continues until the closed end of the article approaches the actuator pad 89. As the article is drawn over the support frame 26 and the belts 38 the article closed end eventually engages the pad 89 and the resultant force is sufficient to cause the latch 90 to disengage and allow linear translation of the shaft 86 toward the limit switch 92. Suitable tensioning of the tubular article occurs before release of the latch 90. Actuation of the limit switch 92 is effective to cause disengagement of the clutch 56 whereupon the drive belts 38 are stopped. After a suitable time delay the actuator 28 is energized to linearly translate the support frame 26 with respect to the frame plate 22 linearly upward, viewing FIG. 2, while the belts 100 continue to rotate. With this action of the apparatus 10 the toroidal rolling of the article 16 is continued until the slide member 29 of the actuator 28 reaches the predetermined limit of its movement. At this point, the rolled article 14 may be held between the peripheral edge of the pad 89 and the idler pulleys on the shafts 42, or the article may be ejected from the support frame 26, depending on the limit position of movement of the actuator 28, the elasticity of the fabric of the article 14 and its tendency to constrict the toroidal roll radially inward.

If the rolled article 14 is ejected off of the pad 89 or is otherwise removed the actuator shaft 86 will then drop into the original position, illustrated in FIG. 5, whereby disengagement of the limit switch 92 will effect actuation of the actuator 28 to return the support 26 and the drive mechanism mounted thereon to the original position illustrated in FIG. 2.

Figure 8:
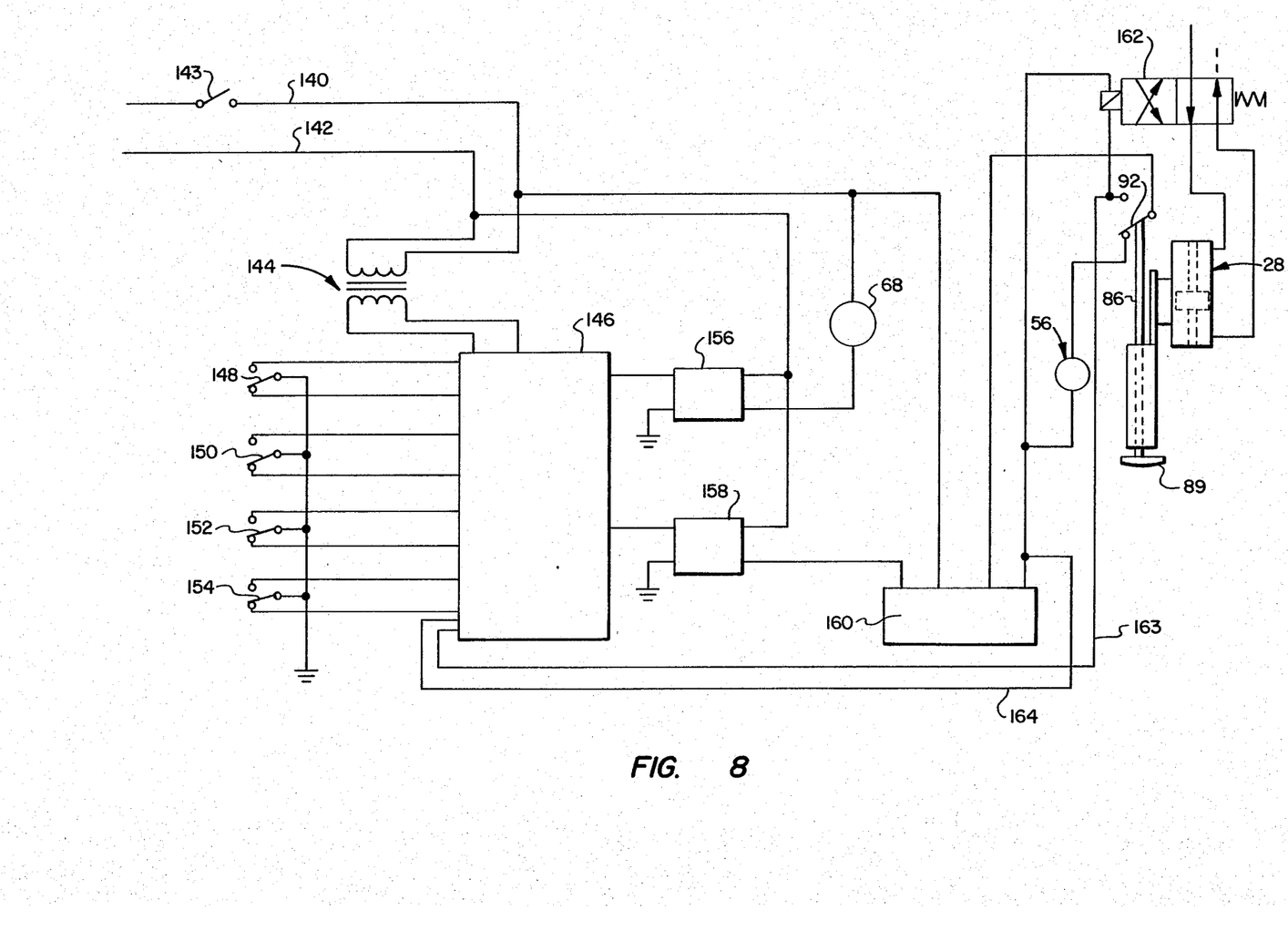
FIG. 8 is a schematic diagram of a control system for the apparatus of the present invention.

Referring now to FIG. 8, there is illustrated a basic schematic diagram of a control circuit for operating the apparatus 10. The control circuit includes conductors 140 and 142 which are adapted to be connected to a source of electric power such as, for example, an alternating current source having a nominal potential of 110 volts. A master switch 143 is interposed in the conductor 140 and a step down transformer 144 is also connected across the conductors for reducing line voltage to a nominal 6.3 volts AC for use in a logic control circuit generally designated by the numeral 146. The control circuit 146 preferably includes four single pole double throw switches 148, 150, 152 and 154 which are suitably interconnected with the logic circuit 146 to condition the circuit to operate the apparatus in a manner to be described herein. The switches 148 through 154 are normally biased in the positions shown. The switch 148, when momentarily thrown from the position shown to the opposite contact position is adapted to condition the circuit 146 to actuate a relay 156 to supply electric power to the motor 68. The circuit 146 is operable to maintain the relay in the condition to conduct electricity to the motor 68 even though the switch 148 is returned to the position indicated in the circuit diagram. The switch 150 is a master off switch which is operable to condition the circuit 146 to shut off the motor 68 and also deenergize a second relay 158 in the event that this relay is conditioned to conduct electric power to a direct current power supply 160.

The power supply 160 is connected to clutch 56 and to a suitable solenoid valve 162 by way of the switch 92, as illustrated. Actuation of switch 152 from its position shown to the alternate position effects actuation of the relay 158 through the circuit 146 to provide a 90 volt DC output from power supply 160 to the circuit including the clutch 56 and the solenoid valve 162. In the normal position of the actuator pad 89, that is when the actuator shaft 86 is latched by the latch 90, the switch 92 is positioned to energize the clutch 56 to drivably connect the clutch driving member with the driven pulley 52. However, when the actuator pad 89 moves the shaft 86 upward as per the orientation of the apparatus shown in FIG. 2, switch 92 moves to the position to connect the valve 162 in circuit with the power supply 160 and deenergize the clutch 56.

Switch 154 is adapted to condition the logic circuit 146 to momentarily effect operation of both relays 156 and 158 to "jog" the apparatus 10. Release of switch 154 to return to its position shown in the circuit diagram will cause logic circuit 146 to deenergize the relay 158 thereby deenergizing the power supply 160 and the circuit components connected thereto.

A typical operating cycle of the apparatus 10 utilizing the control circuit illustrated in FIG. 8 will now be described. Prior to placing a tubular fabric article such as the article 14 over the lower end of the support frame 26 and the drive belts 38, the switch 148 would be momentarily actuated from the position shown to the alternate position to condition the circuit 146 to effect operation of the motor 68 through the relay 156. At this time, however, and until switch 152 is actuated the relay 158 is not effective to connect the electrical source to the power supply 160. Accordingly, the clutch 56 remains deenergized and only the secondary drive belts 100 are being driven by the motor 68. Upon placement of the distal end of the tubular article 14 over the lower end of the support frame 26 the switch 152 is momentarily actuated to condition the logic circuit 146 to energize the relay 158 thereby turning on the power supply 160 and producing an output through switch 92 to energize clutch 56. Energization of clutch 56 to drive the pulley 52 commences driving of the belts 38 to propel the end of the article 14 upward and into engagement with the runs 101 of belts 100 thereby forming the article into a rolled condition.

Upon drawing the article 14 upward so that the closed end of the article engages the pad 89 switch 92 is actuated to move from the position shown in FIG. 8 to the alternate position thereby deenergizing clutch 56 and stopping the drive belts 38. Movement of the switch 92 from the position shown to the alternate position will cause a signal change through conductors 163 and 164, respectively which are connected to the logic circuit 146. A signal change in conductor 164 resulting from deenergization of the clutch 56 will momentarily deenergize the relay 158 turning off the power supply 160. The circuit 146 includes a suitable time delay device which, upon being energized by movement of the switch 92 to the alternate position, will reenergize relay 158 turning on the power supply 160 after a suitable time delay to allow the belts 38 to stop. Upon expiration of the time delay and reenergization of the power supply 160, solenoid valve 162 will be actuated to its alternate position to effect operation of the actuator 28 to move the support frame 26 upwardly. Since belts 100 have continued to run during the aforedescribed sequence of events, upon movement of the support frame 26 with respect to the secondary drive belts, the final rolling of the tubular article will occur and the upward movement of the support frame 26 will also typically effect ejection of the rolled article off of the bottom of the support frame and the actuator pad 89 whereby the article may drop into a suitable receptacle or be handled by an operator.

Removal of the article from the support frame 26 will result in movement of the actuator pad 89 and shaft 86 back to the initial position thereby returning switch 92 to the position shown in FIG. 8. The logic circuit 146, upon sensing a signal change in conductor 163 resulting from movement of the switch 92 from the alternate position toward the position shown in FIG. 8, will cause the relay 158 to deenergize the power supply whereby the apparatus 10 will be conditioned for another operating cycle and the drive belts 38 will be engaged through the clutch 56 only upon actuation of the switch 152.

The provision of the switch 154 is desirable for purposes of momentarily energizing or jogging the apparatus through energization of the relay 158 and subsequently the clutch 56 or the solenoid valve 162, depending on the position of switch 92. Furthermore, when an article 14 is to receive the pull straps 16 the switch 154 may be used to momentarily jog or incrementally commence rolling of the end of the article so that the ends of the straps may be inserted in the rolled end by an operator. The switch 154 may, for example, be a foot operated switch so that both of the operator's hands are free to apply the straps tucked up into the initially rolled portion of the end of the article 14. The switch 150 is operable to condition the logic circuit 146 to effect opening of both relays 156 and 158 thereby effectively shutting down the control circuit entirely.

Those skilled in the art will appreciate from the foregoing description that a unique apparatus has been developed for rolling elongated tubular fabric articles and the like. Although the apparatus is particularly adapted for use in rolling surgical drapes which are formed of an elastic knitted material, referred to in the art as stockinette, other types of tubular fabric articles having open or closed ends may be processed with the apparatus 10. Those skilled in the art will also appreciate that various substitutions and modifications may be made to the apparatus disclosed herein without departing from the scope and spirit of the invention as recited in the appended claims.

What is claimed is:

1. Apparatus for forming an elongated substantially tubular fabric article into a rolled configuration, said tubular article having a closed end at its trailing end relative to its direction of movement, said apparatus including:
   a frame;
   drive means mounted on said frame and including at least a first portion adapted to receive one end of said tubular article in sleeved relationship over and engageable with said first portion of said drive means;
   said first portion of said drive means including elongated flexible means mounted on said frame and engageable with the inner wall surface of said tubular article for pulling said tubular article over and along said first portion of said drive means and over one end of said frame;
   motor means operably connected to said drive means for operating said drive means to pull said tubular article over said first portion of said drive means and into engagement of one end of said tubular article with means operable to cause said one end to roll over onto itself to form said tubular article in a toroidal roll;
   said means engageable with said one end of said tubular article includes a second portion of said drive means including means providing instantaneous linear velocity and engageable with said one end of said tubular article to force said one end generally radially outwardly away from its own longitudinal central axis and then back on the outer wall surface of said tubular article to form said tubular article in a toroidal roll;
   said second portion of said drive means includes endless flexible belt means arranged adjacent respective ones of said elongated flexible means of said first portion;
   said elongated flexible means of said first portion includes respective adjacent pairs of elongated endless belts mounted on respective sets of spaced apart pulleys on said frame;
   said pairs of belts being arranged in a rectangular pattern with longitudinal runs of said belts engageable with said tubular article extending generally parallel to each other, and said means of said second portion engageable with said one end of said tubular article comprises respective endless belts disposed between said belts of each pair of belts of said first portion of said drive means and adapted to engage and turn said end of said tubular article radially outward in response to said tubular article being forced into engagement with said second portion of said drive means;
   said first portion of said drive menas including drivably interconnected shaft means rotatably mounted on said frame and drivenly engaged with at least one pulley of each endless belt;
   said second portion of said drive means including interconnected drive shafts mounted on said frame and drivably connected to said endless belts of said second portion;
   said drive shafts of said first and second portions of said drive means being drivably connected to said motor means through respective drive trains;
   said drive train for said portion of said drive means including clutch means for disengaging said first portion of said drive means from said motor means; and,
   means including an actuating member engageable with a said closed end of said tubular article in response to drawing said tubular article over said first portion of said drive means to effect disengagement of said clutch means to stop said first portion of said drive means in response to engagement of said closed end.

2. The apparatus set forth in claim 1 including:
a first frame part adapted to support said endless flexible means of said first portion of said drive means, and a second frame part adapted to support said second portion of said drive means, and an actuator operably connected to one of said first and second frame parts and operable to effect movement of said first frame part and said first portion of said drive means with respect to said second frame part whereby said drive means is operative to roll said fabric of said tubular article over a last portion of said tubular article toward said closed end.

3. The apparatus set forth in claim 2 wherein:
said actuator comprises a pressure fluid cylinder, and said apparatus includes a control circuit including a switch and valve means responsive to engagement of said actuating means by said closed end to cause said actuator to move said first portion of said drive means relative to said second portion.

4. The apparatus set forth in claim 1 wherein:
said elongated flexible means comprise endless flexible belt means trained over spaced apart pulleys rotatably supported on said frame.

5. The apparatus set forth in claim 4 wherein:
said first portion of said drive means comprises at least four endless belt means arranged on said frame in a rectangular pattern with first longitudinal runs of each of said belt means extending from one end of said frame generally parallel to one another toward said means engageable with said one end.

6. The apparatus set forth in claim 1 wherein:
said first and second portions of said drive means are adapted to provide for a linear velocity of the surface of the second portion of said drive means engageable with said tubular article greater than the linear velocity of the surface of the first portion.

7. The apparatus set forth in claim 1 wherein:
said shaft means include four separate drive shafts arranged in a rectangular pattern with respect to each other and interconnected at one of their respective adjacent ends by bevel gear means.

8. Apparatus for forming an elongated tubular article into a rolled configuration, said tubular article having a closed end at its trailing end relative to its direction of movement, said apparatus including:

a frame including first and second relatively movable parts;

actuator means connected to one of said frame parts for moving said one frame part relative to the other of said frame parts;

drive means mounted on said frame including a first portion mounted on one of said frame parts and adapted to engage said tubular article for moving said tubular article with respect to said one frame part toward a second portion of said drive means mounted on the other of said frame parts, said second portion of said drive means including means for engaging said tubular article for rolling said tubular article back along its tubular sidewall to form said tubular article in a rolled configuration;

means operable upon rolling a portion of said tubular article from one end of said tubular article toward the other end of said tubular article to cause said actuator means to move said frame parts relative to each other to provide for said second portion of said drive means to roll a further portion of said tubular article;

said first portion of said drive means including elongated flexible means mounted on said one frame part and engageable with the inner wall surface of said tubular article for pulling said tubular article over and along said first portion of said drive means and over one end of said one frame part, and said second portion of said drive means including means engageable with said one end of said tubular article to force said one end generally radially outwardly away from its own longitudinal central axis and then back on the outer wall surface of said tubular article to form said tublar article in a toroidal roll; and, an actuating member engageable with said closed end of said tubular article in response to pulling said tubular article over a first portion of said drive means and adapted to stop said first portion of said drive means in response to engagement of said closed end, and to cause said actuator means to move said frame parts relative to each other to provide for said second portions of said drive means to roll said further portion of said tubular article toward said closed end.

* * * * *